United States Patent [19]

Robins et al.

[11] Patent Number: 4,594,414

[45] Date of Patent: Jun. 10, 1986

[54] 2-β-D-RIBOFURANOSYLSELENAZOLE-4-CARBOXAMIDE COMPOUNDS AND METHODS FOR THEIR PRODUCTION

[75] Inventors: Roland K. Robins, Provo, Utah; Prem C. Srivastava, Oak Ridge, Tenn.

[73] Assignee: Brigham Young University, Provo, Utah

[21] Appl. No.: 612,267

[22] Filed: Jun. 22, 1984

Related U.S. Application Data

[60] Division of Ser. No. 465,221, Feb. 15, 1983, Pat. No. 4,531,001, which is a continuation-in-part of Ser. No. 360,968, Mar. 23, 1982, abandoned.

[51] Int. Cl.$^4$ .............................................. C07H 5/04
[52] U.S. Cl. .................................. 536/18.7; 536/121; 536/53; 536/55
[58] Field of Search .................... 536/53, 55, 28, 29, 536/18.7

[56] References Cited

U.S. PATENT DOCUMENTS 4,461,891 7/1984 Robins et al. ..................... 424/180

Primary Examiner—Johnnie R. Brown
Assistant Examiner—Elli Peselev
Attorney, Agent, or Firm—Krass & Young

[57] ABSTRACT

A class of novel 2-β-D-ribofuranosylselenazole-4-carboxamide nucleoside and nucleotide compounds and methods for their production are provided. Compounds of the class typically have pharmacological properties, especially antitumor and antiviral properties, and are well tolerated, being useful, for example, in treating tumors and viral infections in warm blooded animals.

4 Claims, No Drawings

2-β-D-RIBOFURANOSYLSELENAZOLE-4-CARBOXAMIDE COMPOUNDS AND METHODS FOR THEIR PRODUCTION

This application is a division of application Ser. No. 465,221 filed Feb. 15, 1983 now U.S. Pat. No. 4,531,001 which in turn is a continuation-in-part of application Ser. No. 360,968 filed Mar. 23, 1982, now abandoned.

DESCRIPTION

1. Technical Field

This invention is directed to novel 2-β-D-ribofuranosylselenazole-4-carboxamide nucleoside and nucleotide compounds having pharmacological activity, especially antitumor activity and antiviral activity, and to methods for their production.

2. Background of the Invention

Control of malignant tumors in man and animals still remains as an unrealized goal. Within the last several decades, understanding of malignancy has made significant progress; however, conquering of the malignant disease state has not been realized.

Conventional therapy of both humans and other valuable animal species inflicted with malignant tumors presently includes surgicial excising of the tumor, local radiation therapy of the afflicted animal, and chemotherapy by administration of a chemotherapeutic agent to the animal. The death of a significant number of patients inflicted with malignant tumors is attributable not to the primary tumor but instead to metastasis of the primary tumor to secondary sites in the host. If a primary tumor is detected early, it normally can be eliminated by surgery, radiation or chemotherapy or combinations of these. These metastatic colonies of these primary tumors, however, are exceedingly harder to detect and eliminate and the unsuccessful management of them remains a serious medical problem.

Tumors are normally classified either as benign or malignant. The malignant tumor is characterized by its ability to invade both surrounding tissue and to colonize distant sites via metastasis. Certain organs are more prone to metastasis than others. Included in this group would be the lung, the brain, the liver, the ovaries and the adrenal glands. It has further been expected that both surgery and radiation of a primary tumor in certain instances actually promote metastasis.

In view of the inability of current cancer therapy to successfully control the malignant tumor and its metastasis, a need for additional chemotherapeutic agents exists.

Similarly, for the control and management of antiviral infections, agents are currently available, but few are clinically applicable and these are only narrowly active. In this field, therefore, a need for additional chemotherapeutic agents also exists, especially for agents that have both antiviral and antitumor activity.

SUMMARY AND DETAILED DESCRIPTION

The present invention relates to a class of novel chemical compounds and methods for their production, which compounds are 2-β-D-ribofuranosylselenazole-4-carboxamide compounds of the structure I and precursors of the structure II

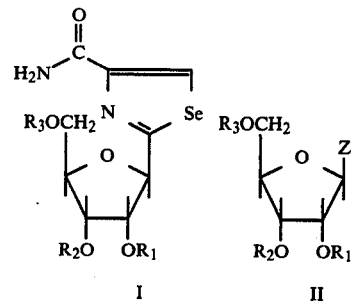

wherein $R_1$ and $R_2$ are each hydrogen or acyl, preferably benzoyl or $C_1$–$C_{18}$ acyl, and $R_3$ is hydrogen, acyl (preferably benzoyl or $C_1$–$C_{18}$ acyl) or

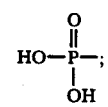

Z is —C(NH$_2$)Se or selenazol-4-(lower alkyl or aralkyl)-carboxylate-2-yl; and, when $R_3$ is phosphono, physiologically acceptable salts thereof.

Preferred compounds, for purposes of the invention are the following:

2-β-D-Ribofuranosylselenazole-4-carboxamide,
2-(2,3,5-Tri-O-acetyl-β-D-ribofuranosyl)-selenazole-4-carboxamide,
2-β-D-Ribofuranosylselenazole-4-carboxamide 5′-phosphate,
2-β-D-Ribofuranosylselenazole-4-carboxamide 5′-phosphate, sodium salt,
2-(2-O-Acetyl-β-D-ribofuranosyl)selenazole-4-carboxamide,
2-(3-O-Acetyl-β-D-ribofuranosyl)selenazole-4-carboxamide,
2-(5-O-Acetyl-β-D-ribofuranosyl)selenazole-4-carboxamide,
2-(2-O-Acetyl-5-O-phosphono-β-D-ribofuranosyl)-selenazole-4-carboxamide,
2-(3-O-Acetyl-5-O-phosphono-β-D-ribofuranosyl)-selenazole-4-carboxamide,
2-(2,3-Di-O-acetyl-β-D-ribofuranosyl)selenazole-4-carboxamide,
2-(2,3-Di-O-acetyl-5-O-phosphono-β-D-ribofuranosyl)-selenazole-4-carboxamide,
2-(2-O-Butyryl-β-D-ribofuranosyl)selenazole-4-carboxamide,
2-(2-O-Benzoyl-β-D-ribofuranosyl)selenazole-4-carboxamide,
2-(2-O-Butyryl-5-O-phosphono-β-D-ribofuranosyl)-selenazole-4-carboxamide,
2-(2-O-Benzoyl-5-O-phosphono-β-D-ribofuranosyl)-selenazole-4-carboxamide,
2-(3-O-Butyryl-5-O-phosphono-β-D-ribofuranosyl)-selenazole-4-carboxamide,
2-(3-O-Benzoyl-5-O-phosphono-β-D-ribofuranosyl)-selenazole-4-carboxamide,
2-(2,3,-Di-O-butyryl-5-O-phosphono-β-D-ribofuranosyl)selenazole-4-carboxamide,
2-(2,3,-Di-O-benzoyl-5-O-phosphono-β-D-ribofuranosyl)selenazole-4-carboxamide,
2-(5-O-Butyryl-β-D-ribofuranosyl)selenazole-4-carboxamide, 2-(5-O-Benzoyl-β-D-ribofuranosyl)selenazole-4-carboxamide, 2-(3-O-Butyryl-β-D-ribofuranosyl)selenazole-4-carboxamide, 2-(3-O-Benzoyl-β-D-ribofuranosyl)selenazole-4-carboxamide, 2,5-Anhydro-3,4,6-tri-O-benzoyl-D-allonselenocarboxamide, Ethyl-2-(2,3,5-tri-O-benzoyl-2-β-D-ribofuranosyl)-selenazole-4-carboxylate.

The latter two compounds exemplify key compounds in the context of the invention that serve for the creation of the unique selenazolecarboxamide nucleus of Structure I.

The compound 2-β-D-ribofuranosylselenazole-4-carboxamide, hereinafter sometimes referred to as COMPOUND 1, has been shown to exhibit significant antitumor activity in vivo and significant antiviral activity in vitro. The present invention in one aspect relates to compositions containing this compound and/or ester derivatives of Structure I in treating tumors in warm blooded animals. According to this aspect of the invention, the antitumor properties of 2-β-D-ribofuranosylselenazole-4-carboxamide and its related esters are utilized by administering to a warm blooded animal an effective amount of a pharmaceutical composition containing as the active ingredient at least about 0.1 percent by weight, based on the total weight of the composition of at least one compound of Structure I.

The present invention in another aspect relates to compositions containing compound 1 and/or ester derivatives of Structure I in treating viral infection in warm blooded animals. According to this aspect of the invention, the antiviral properties of 2-β-D-ribofuranosylselenazole-4-carboxamide and its related esters are utilized by administering to a warm blooded animal an effective amount of a pharmaceutical composition containing as the active ingredient at least about 0.1 percent by weight, based on the total weight of the composition of at least one compound of Structure I.

Specifically noted for $R_1$, $R_2$, and $R_3$ of the compounds of the invention, as preferred acyl groups, are acetyl, propionyl, butyryl, isobutyryl and benzoyl. Noted as preferred salts when $R_3$ is phosphono are the alkali metals and ammonium or substituted ammonium salts such as the sodium, potassium or ammonium salt.

Preferably, when $R_1$ and $R_2$ are each H, $R_3$ is H, $C_1$-$C_8$ acyl or

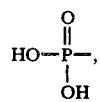

and when $R_1$ and $R_2$ are each $C_1$-$C_8$ acyl, $R_3$ is $C_1$-$C_8$ acyl.

Pharmaceutical compositions of the invention can be formulated in any suitable way, preferably with an inert carrier. Preferably, the pharmaceutical carrier is chosen to allow administration of a suitable concentration of the composition of the invention as a solution or suspension by injection into an afflicted warm blooded animal. Depending on the host harboring the tumor, the type of tumor, and the tumor site, or, depending on the viral infection and type and site of infection, as the case may be, administration by injection may be intravenous, intramuscular, intracerebral, subcutaneous, or intraperitoneal.

Alternatively, the composition of the invention may be formulated in an appropriate pharmaceutical carrier allowing for administration by another route such as oral, ophthalmic, topical or by suppository.

The acyl groups can be selected from a group consisting of straight chain, branch chain, substituted, unsaturated, saturated or aromatic acids such as, but not necessarily limited to, acetic, trifluoroacetic, propionic, n-butyric, isobutyric, valeric, caproic, pelargonic, enanthic, caprylic, lactic, acrylic, propargylic, palmitic, benzoic, phthalic, salicylic, cinnamic and naphthoic acids. With respect to phosphate compounds of the invention, the phosphoryl ester can be as a free acid or as a salt form. Acceptable salts of the phosphate moiety can be selected from, but not necessarily limited to, a group consisting of alkali and alkaline earths, e.g., sodium, potassium, calcium, magnesium and lithium; ammonium and substituted ammonium, including trialkylammonium, dialkylammonium and aklylammonium, e.g., triethylammonium, trimethylammonium, diethylammonium, octylammonium and cetyltrimethylammonium; and cetylpyridinium.

The invention in another aspect relates to a process for the production of ribofuranosylselenazole-4-carboxamide compounds having the described Structure 1. The process comprises:

(a) subjecting an alkyl 2-(2,3,5-tri-O-acyl-β-D-ribofuranosyl)selenazole-4-carboxylate to ammonolysis, (b) phosphorylating 2-β-D-ribofuranosylselenazole-4-carboxamide or a 2'-O-acyl, 3'-O-acyl or 2', 3'-di-O-acyl derivative thereof, (c) acylating 2-β-D-ribofuranosylselenazole-4-carboxamide, (d) de-isopropylidenating 2-(5-O-acyl-2,3-O-isopropylidene-β-D-ribofuranosyl)selenazole-4-carboxamide, or (e) de-tritylating 2-(2-O-acyl-, 3-O-acyl-, or 2,3-di-acyl-5-O-triphenylmethyl-β-D-ribofuranosyl)-selenazole-4-carboxamide.

The ammonolysis reaction, for the production of 2-β-D-ribofuranosylselenazole-4-carboxamide (COMPOUND 1), is carried out in a suitable solvent such as methanol. The reaction conditions can be varied as for example at ambient temperature and pressure, and preferably at room temperature until the reaction is complete, e.g., for about 24 hours. The product is isolated from the reaction mixture in any suitable way such as by column chromatography. The alkyl and acyl groups of the starting material can be varied widely since they are removed in the reaction and thus their choice is not critical. Preferred alkyl groups are $C_1$-$C_8$ alkyl groups. Preferred acyl groups are acetyl, n-butyryl, and benzoyl.

The phosphorylation reaction, for the production of 2-β-D-ribofuranosylselenazole-4-carboxamide 5'-phosphate compounds, is carried out with the mentioned COMPOUND 1 (or a 2'-O-acyl, 3'-O-acyl, or 2',3-di-O-acyl derivative thereof) and a phosphorylating agent such as phosphoryl chloride, advantageously in the cold, in a suitable medium such as triethylphosphate or pyridine and acetonitrile. The product is isolated from the reaction mixture in any suitable way such as by ion-exchange chromatography. Acylation is carried out by reacting COMPOUND 1 with the acylating agent such as an acid anhydride or chloride, preferably in excess at ambient temperature until the reaction is complete. The de-isopropylidenation reaction is carried out by treating the 2-(5-O-acyl-2,3-O-isopropylidene-β-D-ribofuranosyl)selenazole-4-carboxamide with a suitable deprotective agent such as acetic acid, that will selectively remove the isopropylidene group, at elevated temperature until the reaction is complete, e.g. at steam bath temperature for a short period, and isolating the resulting 5'-O-acyl product by a suitable method such as solvent removal and chromatographic work-up of the residue, e.g. using ethyl acetate solvent on silica gel with 20 percent (v/v) ethyl acetate in chloroform eluant. The de-tritylation reaction is carried out similarly by treating 2-(2-O-acyl-, 3-O-acyl-, or 2,3-di-O-acyl-5-O-triphenylmethyl-β-D-ribofuranosyl)selenazole-4-carboxamide with a suitable deprotective agent such as acetic acid, that will selectively remove the trityl group, and by isolating the resulting 2-O-acyl-, 3-O-acyl-, or 2,3-di-O-acyl-β-D-ribofuranosyl)selenazole-4-carboxamide from the reaction mixture by a similar work-up of the residual product after solvent removal.

The invention in another aspect relates to a process for the production of ribofuranosylselenazole-4-carboxamide compounds which comprises producing 2,5-anhydro-3,4,6-tri-O-acyl-D-allonselenocarboxamide of the structure II wherein Z is —C(NH$_2$)Se by reacting 2,3,5-tri-O-acyl-β-D-ribofuranosyl cyanide with liquid hydrogen selenide in the presence of amine catalyst. The catalyst may be a dialkylaminopyridine, preferably 4-dimethylaminopyridine. Acyl moieties, as defined above, of the 2,5-anhydro-3,4,6-tri-O-acyl-D-allonselenocarboxamide may be any of a wide range of alkyl and aromatic acids, preferably acetic or benzoic acids. The reaction is allowed to proceed in a pressure vessel such as a sealed bomb, at ambient temperature and pressure for one to 24 hours. The selenocarboxamides are obtained in pure form by venting the excess hydrogen selenide and subjecting the residue to extraction and chromatography.

The invention in still another aspect relates to a process for the production of ribofuranosylselenazole-4-carboxamide compounds which comprises cyclizing 2,5-anhydro-3,4,6-tri-O-acyl-D-allonselenocarboxamide with a lower (C$_1$-C$_8$) alkyl or aralkyl bromopyruvate(-ROCOCOCH$_2$Br) to obtain an alkyl or aralkyl 2-(2,3,5-tri-O-acyl-β-D-ribofuranosyl)selenazole-4-carboxylate of the structure II wherein Z is a selenazol-4-(lower alkyl or aralkyl)carboxylate-2-yl group. The cyclization reaction is carried out in the cold in a suitable solvent such as acetonitrile or a low boiling alcohol.

The invention and the best mode of carrying out the same are described in the following illustrative examples.

EXAMPLE 1

2-β-Ribofuranosylselenazole-4-Carboxamide, COMPOUND 1

2,5-Anhydro-3,4,6-Tri-O-Benzoyl-D-Allonselenocarboxamide (a) A mixture of 2,3,5-tri-O-benzoyl-β-D-ribofuranosylcyanide (10.0 g, 21.2 mmol), 4-dimethylaminopyridine (200 mg) and liquid hydrogenselenide (condensed under N$_2$ atmosphere, 20 ml) was stirred in a sealed bomb at room temperature for 20 hours. Hydrogen selenide was allowed to evaporate. The dark colored residue was dissolved in chloroform (200 ml) and washed successively with water (3×50 ml), saturated NaHCO$_3$ (3×50 ml) followed by water (2×50 ml). The chloroform portion was dried (MgSO$_4$) and evaporated under vacuum to provide the subtitle product as a foam in almost quantitative yield. The latter product of analytical purity was provided by column chromatography (silica gel, 5 percent ethyl acetate in chloroform). The product developed a purple color when the silica gel chromatogram of the product was sprayed with a dilute ethanolic solution of 2,3-dichloronaphthoquinone and exposed to ammonia.

Analysis calculated for C$_{27}$H$_{23}$NO$_7$Se: C, 58.91; H, 4.21; N, 2.54; Se, 13.98. Found: C, 58.81; H, 4.29; N, 2.51; Se, 13.74.

Reaction of 2,5-Anhydro-3,4,6-Tri-O-Benzoyl-D-Allonseleno-carboxamide with Ethyl Bromopyruvate and the Snythesis of Ethyl 2-(2,3,5-Tri-O-Benzoyl-D-Ribofuranosyl)selenazole-4-Carboxylates (b) A solution of 2,5-anhydro-3,4,6-tri-O-benzoyl-D-allonselenocarboxamide (5.5 g, 10 mmol) in acetonitrile (60 ml) was cooled in ice. Ethylbromopyruvate (3.0 g) in acetonitrile (20 ml) was added dropwise (10 minutes). The ice bath was removed and the reaction mixture was stirred at room temperature for one hour. The solvent was evaporated in vacuo and the residue was triturated with a saturated sodium bicarbonate solution (100 ml) and extracted with ethyl ether (2×100 ml). The combined ether portion was washed with water and dried (MgSO$_4$). The ether was evaporated in vacuo and the residue (syrup) was passed through a silica gel (300 g) column packed in chloroform. Elution with 5 percent ethyl acetate in chloroform provided subtitle products: namely the fast moving ethyl 2-(2,3,5-tri-O-benzoyl-2-β-D-ribofuranosyl)selenazole-4-carboxylate (2.5 g) and the slow moving ethyl 2-(2,3,5-tri-O-benzoyl-2-β-ribofuranosyl)selenazole-4-carboxylate (1.0 g) isolated after evaporation under reduced pressure as thick syrups. The beta isomer, ethyl 2-(2,3,5-tri-O-benzoyl-2-β-D-ribofuranosyl)selenazole-4-carboxylate, is characterized by an optical rotation, 1.07 percent in methanol, $[\alpha]_D^{25} = -34.7°$.

Analysis calculated for C$_{32}$H$_{27}$NO$_9$Se (648.51): C, 59.26; H, 4.20; N, 2.16. Found: C, 59.44; H, 4.21; N, 1.89.

COMPOUND 1

(c) Ethyl 2-(2,3,5-tri-O-benzoyl-β-D-ribofuranoysl-)selenazole-4-carboxylate (3.2 g, 5 mmol) was dissolved in methanol (100 ml), cooled and saturated with ammonia (0 degrees C.). The solution was stirred in a pressure bottle at room temperature for 48 hours. The solvent was evaporated in vacuo and the residue was extracted with chloroform (25 ml×3). The chloroform portion was discarded. The residue was adsorbed on silica gel (10 g) with the help of methanol and applied on a silica gel column (2.8×45 cm) packed in ethyl acetate. The column was eluted with solvent E (ethyl acetate, n-propanol, H$_2$O; 4:1:2; v/v; top layer provides solvent E) and the homogeneous fractions (Rf=0.42, silica gel tlc in solvent E) containing the major product were collected. The solvent was evaporated in vacuo and the title product as a residue was crystallized from 2-propanol: yield 900 mg of the title product, COMPOUND 1, (60 percent) mp 135–136 degrees C. The residue provided a second crop (200 mg) with mp 131–133 degrees C.

Analysis calculated for C$_9$H$_{12}$N$_2$O$_5$Se: C, 35.19; H, 3.94; N, 9.12; Se, 25.71. Found: C, 35.43; H, 3.97; N, 9.03; Se, 25.55; $[\alpha]_D^{25}$, 1.07 percent in methanol, −22.2 degrees.

EXAMPLE 2

2-β-D-Ribofuranosylselenazole-4-Carboxamide 5'-phosphate, COMPOUND 2

Water (151 mg, 8.4 mmol) was added carefully to a solution (maintained at 0 degrees C. by stirring) of phosphoryl chloride (2.0 g, 13.2 mmol), pyridine (1.21 g, 14.4 mmol) and acetonitrile (2.3 g, 56.7 mmol). 2-β-D-Ribofuranosylselenazole-4-carboxamide (921 mg. 3.0 mmol) was added to the solution and the reaction mixture was stirred for 4 hours at 0 degrees C. A clear solution was obtained which was poured into ice water (50 ml) and the pH was adjusted to 2.0 with concentrated sodium hydroxide. The solution was applied to a column of activated charcoal (30 g.), and the column was washed thoroughly with water until the eluate was salt free. The column was eluted with a solution of ethanol-water-concentrated ammonium hydroxide (10:10:1) and the fractions (25 ml each) were collected. The fractions containing the title nucleotide product, COMPOUND 2, in pure form (tlc, silica gel, acetonitrile-0.1N ammonium chloride (7:3) were collected and evaporated to dryness under vacuum. The anhydrous residual product, COMPOUND 2, was dissolved in water and passed through a column of Dowex 50W-X8 (20–50 mesh, H+ form, 15 ml). The column was washed with water and the fraction containing the nucleotide was collected. The solution was concentrated to a small volume (5 ml) and passed through a column of Dowex 50W-X8 (20–50 mesh, Na+ form, 15 ml). The column was washed with water. The fraction containing the nucleotide as the sodium salt was lyophilized. The residue was triturated with ethanol collected by filtration and dried ($P_2O_5$), to provide 580 mg (42 percent) of 2-β-D-ribofuranosylselenazole-4-carboxamide 5'-phosphate as monosodium trihydrate in the crystalline form.

Analysis calculated for $C_9H_{12}N_2O_8PSeNa.3H_2O$: C, 23.33; H, 3.90; N, 6.05; P, 6.69; Se, 17.04. Found: C, 23.01; H, 3.76; N, 5.86; P, 7.02; Se, 16.32.

EXAMPLE 3

2-(2,3,5-Tri-O-Acetyl-β-D-Ribofuranosyl)selenazole-4-Carboxamide, COMPOUND 3

A mixture of 2-β-D-ribofuranosylselenazole-4-carboxamide (1.0 g, 3.25 mmol), N,N-dimethylaminopyridine (catalyst, 80 mg) and acetic anhydride (15 ml) was stirred at room temperature for 3 hours. The solvent was evaporated in vacuo and coevaporated with water (10 ml×2) to provide COMPOUND 3 as a white crystalline product which was triturated with water and collected by filtration. The product was recrystallized from water containing a few drops of ethanol to provide white needles: yield 1.2 g (85 percent), mp 117–119 degrees C.

Analysis calculated for $C_{15}H_{18}N_2O_8Se$: C, 41.58; H, 4.19; N, 6.47; Se, 18.22. Found: C, 41.80; H, 4.30; N, 6.58; Se, 17.97. Corresponding 2',3',5'-O-acyl compounds of the invention are prepared from COMPOUND 1 by this procedure by reacting the latter with the appropriate acid anhydride until the reaction is complete and isolating the product in pure form.

EXAMPLE 4

2-(5-O-Acetyl-β-D-ribofuranosyl)selenazole-4-carboxamide

2-β-D-ribofuronosylselenazole-4-carboxamide is first isopropylidenated with 2,2-dimethoxypropane, 70 percent perchloric acid and acetone to selectively protect the 2',3'-hydroxyls and then the 5'-hydroxyl is acetylated with acetic anhydride in pyridine as in Example 3 to provide 2-(5-O-acetyl-2,3-O-isopropylidene-β-D-ribofuranosyl)selenazole-4-carboxamide. Selective removal of the acid sensitive isopropylidene group with 80 percent acetic acid and purification by chromatography provides 2-(5-O-acetyl-β-D-ribofuranosyl)-selenazole-4-carboxamide as a crystalline solid.

EXAMPLE 5

2-(2-O-Acetyl-β-D-ribofuranosyl)selenazole-4-carboxamide and 2-(3-O-Acetyl-β-D-ribofuranosyl(selenazole-4-carboxamide 2-β-D-ribofuranosylselenazole-4-carboxamide in pyridine is successively treated first with one molar equivalent of triphenylmethyl chloride and then with one equivalent of acetic anhydride to provide a mixture of the 5'-O-tritylated title products which, after chromatographic purification, afford the separate products 2-(2- and 3-O-acetyl-5-O-triphenylmethyl-β-D-ribofuranosyl)selenazole-4-carboxamide as pure oils. Detritylation of 2-(2-O-acetyl-5-O-triphenylmethyl)-selenazole-4-carboxamide with 80 percent acetic acid affords 2-(2-O-acetyl-β-D-ribofuranosyl)selenazole-4-carboxamide as a crystalline solid.

2-(3-O-Acetyl-β-D-ribofuranosyl)selenazole-4-carboxamide in crystalline form is prepared in like manner from the corresponding 5'-O-tritylated product.

EXAMPLE 6

2-(2,3-Di-O-acetyl-β-D-ribofuranosyl)selenazole-4-carboxamide 2-(5-O-Triphenylmethyl-β-D-ribofuranosyl)-selenazole-4-carboxamide prepared by the procedure of Example 5 in which COMPOUND 1 in pyridine is treated with an equivalent of triphenylmethyl chloride is treated with excess acetic anhydride in pyridine. The resulting 2',3'-di-O-acetyl product is isolated and detritylated as in Example 5. Chromatagraphic purification of the reaction mixture provides the title product, 2,3-di-O-acetyl-β-D-ribofuranosyl)selenazole-4-carboxamide in pure form as a hard foam.

EXAMPLE 7

2-(5-O-Butyrl-β-D-ribofuranosyl)selenazole-4-carboxamide and 2-(5-O-Benzoyl-β-D-ribofuranosyl)selenazole-4-carboxamide Each of these 5'-acid esters is prepared in a fashion analogous to the procedure of Example 4 using COMPOUND 1 as a starting material. Thus the starting material is 2',3'-O-isopropylidenated and the 5'-hydroxyl group of the resulting 2',3'-O-isopropylidene compound is monoacylated using n-butyric anhydride and benzoic anhydride, respectively. Selective removal of the acid sensitive isopropylidene group with 80 percent acetic acid and purification by chromatography provides each of the respective title compounds in pure form.

EXAMPLE 8

2-(2-O-Butyryl-β-D-ribofuranosyl)selenazole-4-carboxamide, 2-(2-O-Benzoyl-β-D-ribofuranosyl)selenazole-4-carboxamide, 2-(3-O-Butyryl-β-D-ribofuranosyl)selenazole-4-carboxamide, 2-(3-O-Benzoyl-β-D-ribofuranosyl)selenazole-4-carboxamide Each of these acid esters of 2-β-D-ribofuranosylselenazole is prepared by the procedure illustrated in Example 5. Thus COMPOUND 1 in pyridine is 5'-O-tritylated, the resulting O-trityl compound is monoacylated with either n-butyric anhydride or benzoic anhydride as required, and the resulting mixture of 2'- and 3'-O-actyl-5-O-trityl products subjected to chromatographic purification to provide the separate 2-(2- and 3-O-acyl-5-O-triphenylmethyl-β-D-ribofuranosyl)-selenazole-4-carboxamides in pure form. Detritylation of the respective 2-(2- or 3-O-acyl-5-O-triphenylmethyl)selenazole-4-carboxamide with 80 percent acetic acid gives the corresponding title product as a crystalline solid.

EXAMPLE 9

2-(2,3-Di-O-butyryl-β-D-ribofuranosyl)selenazole-4-carboxamide and 2-(2,3-Di-O-benzoyl-β-D-ribofuranosyl)-selenazole-4-carboxamide Each of these di-acid esters of 2-β-D-ribofuranosylselenazole-4-carboxamides is prepared from 2-(5-O-triphenylmethyl-β-D-ribofuranosyl)selenazole-4-carboxamide using excess n-butyric anhydride and benzoic anhydride, respectively, in pyridine by the procedure described in Example 6.

EXAMPLE 10

2-(2-O-Acetyl-5-O-phosphono-β-D-ribofuranosyl)-selenazole-4-carboxamide 2-(2-O-Acetyl-β-D-ribofuranosyl)selenazole-4-carboxamide is treated with 1 to 5 equivalents of phosphoryl chloride in the presence of triethylphosphate at 0 degrees C. Afer complete dissolution is obtained, the solution is poured over crushed ice and adjusted with sodium hydroxide solution to pH 7, extracted with chloroform, and placed on a column of ion exchange resin (Dowex AG 1×8, formate). The column is first washed with water, then the product is eluted with a gradient of water-formic acid. The fractions containing pure product are pooled and evaporated to dryness. The residue is recrystallized from ethanol-water to provide the free acid of the title compound as a crystalline solid.

EXAMPLE 11

2-(2-O-Butyryl-5-O-phosphono-β-D-ribofuranosyl)-selenazole-4-carboxamide 2-(2-O-Benzoyl-5-O-phosphono-β-D-ribofuranosyl)-selenazole-4-carboxamide 2-(3-O-Butyryl-5-O-phosphono-β-D-ribofuranosyl)-selenazole-4-carboxamide 2-(3-O-Benzoyl-5-O-phosphono-β-D-ribofuranosyl)-selenazole-4-carboxamide 2-(2,3-Di-O-acetyl-5-O-phosphono-β-D-ribofuranosyl)-selenazole-4-carboxamide 2-(2,3-Di-O-butyryl-5-O-phosphono-β-D-ribofuranosyl)selenazole-4-carboxamide 2-(2,3-Di-O-benzoyl-5-O-phosphono-β-D-ribofuranosyl)selenazole-4-carboxamide The title compounds in pure form are each prepared by the procedure described in Example 10 by treating the corresponding 5'-hydroxyl compound with phosphoryl chloride in the presence of triethyl phosphate at 0 degrees C.; followed by appropriate work-up of the reaction mixture, as described, to provide the free acid as a crystalline solid.

As illustrative examples of the antitumor use of COMPOUNDS 1 and 2, Examples 12 through 14, below, are given. In these examples, the efficacy of the compounds is demonstrated using standard tests against a tumor, Lewis lung carcinoma. The tests utilized in these illustrative examples were conducted by the Developmental Therapeutics Program, Division of Cancer Treatment, National Cancer Institute. The tests were supervised by this agency utilizing their standard protocols and procedures. All tests conformed to these protocols and all tests were evaluated under the criteria defined by these protocols. The following representative examples illustrate confirmed activity of the illustrative compounds of the invention against screening tumor systems of the National Cancer Institute.

For purposes of the following examples, the abbreviation IP stands for intraperitoneal and IV stands for intravenous. The mean and median survival times are calculated in instruction 14 (revised 6/78) of the Screening Data Summary, Developmental Therapeutics Program, Division of Cancer Treatment, National Cancer Institute. The contents of this Screening Data Summary including appropriate revisions are herein incorporated by reference.

In the illustrated examples below, the vehicle used as carrier for the drug was injected (minus any drug therein) into the control animals at the same level of use of the vehicle in the drug treated animals in order to eliminate any vehicle effect of the tests.

2-β-D-Ribofuranosylselenazole-4-carboxyamide, COMPOUND 1, is indicated as being active against Lewis lung carcinoma as per Example 12 and successfully passed the DN (decision network) 2 criteria of the National Cancer Institute Testing. For example 12, $B_6D_2F_1$ male mice were used and challenged with Lewis lung carcinoma. The median survival time of the test animals was compared to that of appropriate control animals. Based on this criterion COMPOUND 1 was considered as an effective antitumor agent.

In Example 12, forty control animals and ten test animals were used, each at dose levels indicated below in Table 1. For both the control group and the drug treated group, tumors were induced by IV injection on day zero followed by initiation of drug treatment on day one. For Example 12 water was used as the drug vehicle.

In both the control group and the drug treated group in Example 12, the animals were inoculated on day zero with a homogenate of $10^6$ seed cells of Lewis lung carcinoma. For Example 12, drug treatment was started on day one and COMPOUND 1 given once daily for nine days. Day five was utilized as the cut-off date for deaths attributable to toxicity of the drug. There was no mortality attributable to drug toxicity in this example. Efficacy of treatment was determined by comparing median survival time of the control animals and is expressed as percentage increase of treated animals/control animals (T/C).

The test period was for sixty days and at the end of the sixty day period all animals surviving in the test groups were evaluated as either cured, no-takes, or tumor survivors.

EXAMPLE 12

In this example, the drug tested animals were injected IP with the dose level noted in Table I below. Ten animals were treated at each dose level. No control animals survived beyond day 23 with a median death date of day 19.0. At dose levels of 75 and 13 mg/kg, all of the treated animals survived, giving a T/C of 315 percent and 7 out of 10 and 5 out of 10 cures, respectively. Furthermore, at the relative low dose of 3 mg/kg, DN2 criteria of NCI were passed by achievement of T/C of 152 percent. One cure was achieved at this dose level.

COMPOUND 1 is indicated as being an active antitumor agent in the multiple dose studies noted.

TABLE 1

Antitumor Activity - COMPOUND 1

| Drug Dose mg/kg | Treated Group Survival Time | Control Group Survival Time | Cures | Percent Treated Animals/ Control Animals |
|---|---|---|---|---|
| 75 | 60.0 | 19.0 | 7/10 | 315% |
| 50 | 18.0 | | 1/10 | 94% |
| 33 | 18.0 | | 3/10 | 94% |
| 20 | 16.0 | | 2/10 | |
| 13 | 60.0 | | 5/10 | 315% |
| 9 | 10.4 | | 3/10 | |
| 6 | 12.0 | | 1/10 | |
| 3 | 28.9 | | 1/10 | 152% |

As is shown in Table I, COMPOUND 1 shows outstanding activity against Lewis lung carcinoma. Lewis lung carcinoma is an excellent example of a metastatic tumor system. The test animals and control animals of Example 12 were inoculated IV with a homogenate of the tumor. Dramatic expression of this tumor is then seen in the lungs. The ability to metastasize is a property that uniquely characterizes a malignant tumor from a benign tumor.

EXAMPLE 13

In this example COMPOUND 1 was tested in $B_6D_2F_1$ female mice challenged with Lewis lung carcinoma. The median survival time of the test animals was compared to that of appropriate control animals. Based on this criterion COMPOUND 1 was found to be an effective antitumor agent as shown in Table II. At dose levels of 50, 25, and 12.50 mg/kg all of the test animals survived, giving a T/C of 355 percent; 6 out of 10, 7 out of 10, and 8 out of 10 cures were achieved, respectively.

TABLE II

Antitumor Activity - COMPOUND 1

| Drug Dose mg/kg | Treated Group Survival Time | Control Group Survival Time | Cures | Percent Treated Animals/ Control Animals |
|---|---|---|---|---|
| 200 | 10.7 | 16.9 | 0/10 | |
| 100 | 20.3 | | 3/10 | 120 |
| 50 | 60.0 | | 6/10 | 355 |
| 25 | 60.0 | | 7/10 | 355 |
| 12 | 60.0 | | 8/10 | 355 |

COMPOUND 1 was further tested in a Lewis lung in vivo mouse model using $B_6D_2F_1$ female mice challenged with Lewis lung carcinoma. The results are set forth in Table III. As shown, COMPOUND 1 at low dose levels (24, 12 and 6 mg/kg) had a T/C of 297 percent; 9 out of 10, 9, out of 10, and 5 out of 10 cures were achieved, respectively. COMPOUND 1 achieved DN2 level activity (percent T/C greater than 150) of 153 at the low dose of 3 mg/kg. The results confirm that COMPOUND 1 is an effective antitumor agent for Lewis lung carcinoma in mice.

TABLE III

Antitumor Activity - COMPOUND 1

| Drug Dose mg/kg | Treated Group Survival Time | Control Group Survival Time | Cures | Percent Treated Animals/ Control Animals |
|---|---|---|---|---|
| 24.00 | 60.0 | 20.2 | 9/10 | 297 |
| 12.00 | 60.0 | | 9/10 | 297 |
| 6.00 | 60.0 | | 5/10 | 297 |
| 3.00 | 31.0 | | 0/10 | 153 |
| 1.50 | 22.3 | | 0/10 | 110 |
| 0.75 | 21.7 | | 0/10 | 107 |

EXAMPLE 14

COMPOUND 2, 2-(5-phosphono-$\beta$-D-ribofuranosyl)selenazole-4-carboxamide was screened for lewis lung carcinoma activity in a manner similar to that described in Example 12. In this example, $B_6D_2F_1$ male mice were challenged with Lewis lung carcinoma. The mean survival time of the test animals was compared to that of appropriate control animals. Based on this criterion, COMPOUND 2 was considered to be an effective antitumor agent. In this example, cures ranging from 1 out of 10 to 4 out of 10 treated mice were obtained at a dose ranging from 9 mg/kg to 75 mg/kg, Table IV below. At 13 mg/kg the treated, surviving mice have a T/C of 315 percent and 4 out of 10 cures were achieved.

TABLE IV

Antitumor Activity - COMPOUND 2

| Drug Dose mg/kg | Treated Group Survival Time | Control Group Survival Time | Cures | Percent Treated Animals/ Control Animals |
|---|---|---|---|---|
| 75 | 15.5 | 19.0 | 1/10 | |
| 50 | 12.5 | | 3/10 | |
| 33 | 12.5 | | 3/10 | |
| 20 | 12.0 | | 2/10 | |
| 13 | 60.0 | | 4/10 | 315 |
| 9 | 12.5 | | 1/10 | |
| 6 | 22.0 | | 0/10 | 115 |
| 3 | 20.8 | | 0/10 | 109 |

In further tests, growth-inhibitory effects of COMPOUND 1 and COMPOUND 2 were measured against 3 mouse tumor lines in suspension cell culture. Cell cultures were initiated at a density of 50,000 cells/ml in medium RPMI 1630 supplemented with 10 percent fetal calf serum. Composition of this culture medium and details of the culture procedure followed the published method (G. E. Moore, A. A. Sandberg and K. Ulrich, Suspension Cell Culture and in vivo and in-vitro chromosome constitution of mouse leukemia L1210, Journal of the National Cancer Institute 36, 405-415, 1966). Cultures were maintained at 37 degrees in stationary suspension culture under a 95 percent air+5 percent $CO_2$ atmosphere. Test compounds were added to treated cultures at the time of initiation, and were present continually. After 72 hours, 40-fold dilutions of drug-treated and untreated control cultures were prepared in 0.9 percent NACl solution, and cells were counted on an electronic particle counter. The results of the tests are shown in Table V below. The growth-inhibitory effects are expressed as $ID_{50}$ values, namely, test compound inhibitory dosages or concentrations required to decrease cell count in treated cultures to 50 percent of the cell count of untreated control cultures.

TABLE V

| $ID_{50}$ Values (Molar) Against Various Tumor Cell Lines | | | |
|---|---|---|---|
| | L-1210 | P388 | $B_{16}$ Melanoma |
| COMPOUND 1 | $4.0 \times 10^{-7}$ | $2.7 \times 10^{-7}$ | $3.5 \times 10^{-6}$ |
| COMPOUND 2 | $5.8 \times 10^{-8}$ | $6.6 \times 10^{-8}$ | $7.5 \times 10^{-6}$ |

These results show that COMPOUND 1 and COMPOUND 2 both inhibit growth in cell culture for representative tumor lines at extremely low dosage. In this regard, the 5'-phosphate (COMPOUND 2) appears to be superior to COMPOUND 1.

EXAMPLE 15

In one embodiment, COMPOUND 1 showed activity against both small and large viruses of both DNA and RNA types by the virus rating (VR) method of Sidwell et al., Appl. Microbiol. 22, 797 (1971). A virus rating that is greater than 1.0 indicates definite antiviral activity. A virus rating of 0.5–0.9 indicates moderate antiviral activity, and a virus rating smaller than 0.5 suggests slight or no apparent antiviral activity. The results reported below were obtained by testing on Microtest II (Falcon Plastics) plastic panels with a monolayer of Vero or HeLa cells.

| ANTIVIRAL ACTIVITY OF COMPOUND 1 | | | | |
|---|---|---|---|---|
| | Virus Rating | | $ED_{50}$ (ug/ml) | |
| Virus | Vero | HeLa | Vero | HeLa |
| RNA viruses | | | | |
| Para 3 | 2.6 | 2.2 | 1 | 1 |
| Measles | 2.0 | 1.8 | 1 | 2 |
| Mumps | 1.7 | 1.0 | 5 | 1 |
| Reo 3 | 1.8 | 2.7 | 1 | 8 |
| VSV | 0.4 | 2.1 | 1000 | 9 |
| Cox B1 | 1.7 | 1.8 | 15 | 10 |
| Cox B4 | 0.0 | 2.3 | 1000 | 6 |
| DNA viruses | | | | |
| VV | 2.1 | 2.4 | 3 | 2 |
| Ad-2 | — | 1.9 | — | 9 |
| HSV-1 | 1.2 | 1.4 | 30 | 2 |
| HSV-2 | 1.5 | 1.5 | 10 | 4 |

The results indicate that COMPOUND 1 has good broad spectrum antiviral activity against both DNA and RNA viruses. From the DNA viruses, the representatives of the families Poxviridae (Vaccinia) and Herpesviridae (HSV-1, HSV-2) were inhibited most. Greatest activity was observed in the representatives of RNA families Paramyxoviridae (Para-3, Mumps, Measles) and Reoviridae (Reo-3). Excellent antiviral activity was measured in Heha cells for the families Adenoviridae (Adeno-2), Picornaviridae (Cox B1, Cox B4) and Rhabdoviridae (VSV).

The studies further indicate that antiviral activity of COMPOUND 1 is both virucidal (against Vaccinia) and virusstatic (against Para-3 and HSV-1), depending upon the virus and cell line used. Also, the prophylactic use of COMPOUND 1 may enhance its antiviral activity against virustatic species such as HSV-1. COMPOUND 1 is non-toxic to Vero, Hela and MRC-5 cells in 1000 ug/ml quantities (highest concentration tested).

These results further show that COMPOUND 1 inhibits viral cytopathic effects in cell culture for representative viruses at extremely low dosage; COMPOUND 1 exhibits low cytotoxicity and is soluble in aqueous media.

The following representative examples 16 through 20, are given as illustrative pharmaceutical compositions utilizing different carriers. In these examples, example 16 illustrates the use of the compounds of the invention in injectables suitable for intravenous or other types of injection into the host animal. Example 17 is directed to an oral syrup preparation, Example 18 to an oral capsule preparation and Example 19 to oral tablets. Example 20 is directed to use of the compounds of the invention in suitable suppositories. For example 16 through 20, the ingredients are listed followed by the methods of preparing the compositions.

EXAMPLE 16

INJECTABLES

Example 16a

COMPOUND 1

| COMPOUND 1 | 125 mg–500 mg |
|---|---|

Water for Injection USP q.s.

COMPOUND 1 is dissolved in the water and passed through a 0.22 micron filter. The filtered solution is added to ampoules or vials, sealed and sterilized.

Example 16b

COMPOUND 2

COMPOUND 2 as a Sodium Salt 125 mg–500 mg

Water for Injection USP q.s.

Prepared as per Example 16a above.

EXAMPLE 17

SYRUP

Example 17a

COMPOUND 1

| 125 mg Active ingredient/5 ml syrup | |
|---|---|
| COMPOUND 1 | 25 g |
| Purified Water USP | 200 ml |
| Cherry Syrup q.s. ad | 1000 ml |

COMPOUND 1 is dissolved in the water and to this solution the syrup is added with mild stirring.

Example 17b

COMPOUND 2

| 125 mg Active Ingredients/5 ml syrup | |
|---|---|
| COMPOUND 2 as a Sodium Salt | 25 g |
| Purified Water USP q.s. or | 200 ml |
| Cherry Syrup q.s. ad | 1000 ml |

Prepared as per Example 17a above.

EXAMPLE 18

CAPSULES

Example 18a

COMPOUND 1

| 50 mg, 125 mg or 250 mg | |
|---|---|
| COMPOUND 1 | 500 g |
| Lactose USP, Anhydrous q.s. or | 200 g |
| Sterotex Powder HM | 5 g |

Combine COMPOUND 1 and the Lactose in a twin-shell blender equipped with an intensifier bar. Tumble blend for two minutes, blend for one minute with the intensifier bar and then tumble blend again for one minute. A portion of the blend is then mixed with the Stereotex Powder, passed through a #30 screen and added back to the remainder of the blend. The mixed ingredients are then blended for one minute, blended with the intensifier bar for thirty seconds and tumble blended for an additional minute. Appropriate sized capsules are filled with 141 mg. 352.5 mg or 705 mg of the blend, respectively, for the 50 mg., 125 mg and 250 mg containing capsules.

Example 18b

COMPOUND 2

| 50 mg, 125 mg or 250 mg | |
|---|---|
| COMPOUND 2 | 500 g |
| Lactose USP, Anhydrous q.s. or | 200 g |
| Sterotex Powder HM | 5 g |

Mix and fill as per Example 18a.

EXAMPLE 19

TABLETS

| 50 mg, 100 mg or 250 mg | |
|---|---|
| COMPOUND 1 | 250 g |
| Corn Starch NF | 200.0 g |
| Cellullose, Microcrystalline | 46.0 g |
| Sterotex Powder HM | 4.0 g |
| Purified Water q.s. or | 300.0 ml |

Combine the corn starch, the cellulose and COMPOUND 1 together in a planetary mixer and mix for two minutes. Add the water to this combination and mix for one minute. The resulting mix is spread on trays and dried in a hot air oven at 50 degrees C. until a moisture level of 1 to 2 percent is obtained. The dried mix is then milled with a Fitzmill through a #RH2B screen at medium speed. The Sterotex Powder is added to a portion of the mix and passed through a #30 screen, and added back to the milled mixture and the total blended for five minutes by drum rolling. Compressed tablets of 150 mg. 375 mg and 750 mg respectively, of the total mix are formed with appropriate sized punches for the 50 mg, 125 mg or 500 mg containing tablets.

EXAMPLE 20

SUPPOSITORIES

EXAMPLE 20a

COMPOUND 1

| 125 mg. 250 mg or 500 mg per 3 g | | | |
|---|---|---|---|
| COMPOUND 1 | 125 mg | 250 mg | 500 mg |
| Polyethylene Glycol 1540 | 1925 mg | 1750 mg | 1400 mg |
| Polyethylene Glycol 8000 | 825 mg | 750 mg | 600 mg |

Melt the Polyethylene Glycol 1540 and the Polyethylene Glycol 8000 together at 60 degrees C. and dissolve COMPOUND 1 into the melt. Mold this total at 25 degrees C. into appropriate suppositories.

Example 20b

COMPOUND 2

| 125, 250, 500 MG PER 3 G | | | |
|---|---|---|---|
| COMPOUND 2 | 125 mg | 200 mg | 500 mg |
| Polyethylene Glycol 1540 | 1925 mg | 1750 mg | 1400 mg |
| Polyethylene Glycol 8000 | 825 mg | 750 mg | 600 mg |

Prepare as per Example 20a above.

The embodiments of the invention in which an exclusive property or privilege is claimed are defined as follows:

1. A compound of the structure II:

$$\text{Structure II}$$

with substituents $R_3OCH_2$, $R_2O$, $OR_1$, and $Z$ on the furanose ring.

wherein $R_1$, $R_2$ and $R_3$ are acyl selected from the group consisting of benzoyl and $C_1$ to $C_{18}$ acyl; and Z is $-C(NH_2)Se$.

2. A compound according to claim 1 which is a 2,5-anhydro-3,4,6-tri-O-acyl-D-allonselenocarboxamide.

3. A compound according to claim 2 which is 2,5-anhydro-3,4,6-tri-O-benzoyl-D-allonselenocarboxamide.

4. A process for the production of compounds according to claim 1 which comprises producing 2,5-anhydro-3,4,6-tri-O-acyl-D-allonselenocarboxamide of the structure II by reacting 2,3,5-tri-O-acyl-B-D-ribofuranosyl cyanide with liquid hydrogen selenide in the presence of amine catalyst.

* * * * *

UNITED STATES PATENT AND TRADEMARK OFFICE
CERTIFICATE OF CORRECTION

PATENT NO. : 4,594,414

DATED : June 10, 1986

INVENTOR(S) : Robins et al.

It is certified that error appears in the above-identified patent and that said Letters Patent is hereby corrected as shown below:

Column 3, line 40 "0.1" should be --1.0--.

Column 9, line 38 "Afer" should be --After--.

Column 11, line 33 "the test animals and control animals" should be --the tests and control animals--.

Column 11, line 68 "9 out of 10, 9, out of 10" should be --9 out of 10, 9 out of 10--.

Column 12, line 23 "lewis" should be --Lewis--.

Column 12, line 24 "$B6_C2_F1$" should be --$B_6D_2F_1$--.

Column 13, line 56 "Heha" should be --Hela--.

Column 14, line 16 "example" should be --Examples--.

Column 15, line 19 "stereotex" should be --Sterotex--.

Column 15, line 44 "cellullose" should be --cellulose--.

Signed and Sealed this

Fourteenth Day of October, 1986

[SEAL]

Attest:

DONALD J. QUIGG

Attesting Officer

Commissioner of Patents and Trademarks